United States Patent [19]

Donhauser et al.

[11] Patent Number: 4,755,295
[45] Date of Patent: Jul. 5, 1988

[54] MULTISTAGE ARRANGEMENT FOR COUNTERCURRENT SEPARATION AND METHODS OF OPERATING SAME

[75] Inventors: Friedrich Donhauser, Amberg; Anton Schoengen, Witten; Johann H. Shroeder, Dortmund; Jörg Porschen, Düren, all of Fed. Rep. of Germany

[73] Assignees: Amberger Kaolinwerke GmbH; Dynamit Nobel AG

[21] Appl. No.: 80,746

[22] Filed: Jul. 31, 1987

Related U.S. Application Data

[62] Division of Ser. No. 948,049, Dec. 31, 1986, Pat. No. 4,707,274.

[30] Foreign Application Priority Data

Jan. 10, 1986 [DE] Fed. Rep. of Germany ....... 3600522
Feb. 27, 1986 [DE] Fed. Rep. of Germany ....... 3606259
Nov. 22, 1986 [DE] Fed. Rep. of Germany ....... 3639958

[51] Int. Cl.$^4$ .......................................... B01D 17/038
[52] U.S. Cl. ................................. 210/512.2; 209/144; 209/211
[58] Field of Search ............... 210/774, 175, 787, 788, 210/808, 512.2, 304; 209/144, 211

[56] References Cited

U.S. PATENT DOCUMENTS

| | | | |
|---|---|---|---|
| 4,285,706 | 8/1981 | Dehne | 210/512.2 |
| 4,455,224 | 6/1984 | Kaiser | 210/512.2 |
| 4,601,734 | 7/1986 | Meier et al. | 210/152.2 |

*Primary Examiner*—Frank Sever
*Attorney, Agent, or Firm*—Toren, McGeady & Associates

[57] ABSTRACT

A multistage arrangement for countercurrent separation of suspended solids, such as crystals, by means of hydro-cyclone groups connected in series and corresponding pumps and pump wells. For operating with relatively small expenditures with respect to apparatus under high pressures and at high temperatures within a certain, limited temperature range, the hydro-cyclone groups, the pump wells with pumps projecting into the pump wells, and the essential parts or regions of the lines are placed in a common pressure-proof and heat-insulated chamber. In addition, for removing coarser crystallizations and solid particles, an upstream classifier also accommodated in the chamber may be provided. The multistage arrangement can be used in a process for the production of terephthalic acid from dimethyl-terephthalate as the intermediate product, and in a process for the hydrogenation of coal.

24 Claims, 9 Drawing Sheets

MULTISTAGE ARRANGEMENT FOR COUNTERCURRENT SEPARATION AND METHODS OF OPERATING SAME

This is a division of application Ser. No. 948,049, filed Dec. 31, 1986 now U.S. Pat. No. 4,707,274.

BACKGROUND OF THE INVENTION

1. Field of the Invention

The present invention relates generally to multistage arrangements for countercurrent washing or countercurrent separation. The invention relates particularly to a multistage arrangement for countercurrent separation of suspended solids, particularly crystals, by means of hydro-cyclones arranged in series one behind the other, by means of groups of several hydro-cyclones connected in parallel. The arrangement further includes pumps and pump wells and pipe lines connecting the aforementioned structural elements. In this arrangement, the washing or separating fluid is conducted in a countercurrent against the feed direction of the suspended solids and the suspended solids are treated under increased pressure and temperature.

2. Description of the Prior Art

The principal construction and the corresponding mathematical bases of such arrangements are described in "Verfahrenstechnik 8 (1974), No. 1 pages 28–31" and in the "Aufbereitungstechnik", 18th year (1977), pages 395–404. Such arrangements are also discussed in German Patent No. 30 44 617, which relates to a process for the production of terephthalic acid from dimethyl-terephthalate as an intermediate product. Further, a countercurrent separating unit is disclosed in German Patent No. 29 16 197.

In such countercurrent separators, dissolved impurities are to be separated. These impurities of the feeding suspension lie below the separation grain boundary of the hydro-cyclone. The separating fluid functioning for their separation can be of different types. For example, for this purpose, demineralized water is used. One of the considerable advantages of the hydro-cyclone known for this purpose is the fact that the solid matters present in the feeding suspension are classified and are fed corresponding to their classification to the overflow or underflow.

In many fields of application, the requirement is that the process must be operated under increased pressure and temperature. Due to process conditions, a certain range of temperature must be maintained.

It is, therefore, a primary object of the present invention to further develop an arrangement of the type described above. It is specifically an object of the present invention to provide an arrangement of the above-described type in which the cost required for the apparatus is as low as possible.

SUMMARY OF THE INVENTION

In accordance with the present invention, in a multistage arrangement for countercurrent separation of the above-described type, the hydro-cyclones or hydro-cyclone groups and pump wells forming part of the arrangement including pumps or pump components projecting into the pump wells are placed in a common pressure-proof and heat-insulated chamber or vessel.

In accordance with a preferred embodiment of the invention, all essential parts of the arrangement, particularly the greater part of the connecting pipe lines, are also placed in the pressure-proof and heat-insulated chamber. This serves to ensure the safety of the persons working with the arrangement. In addition, heat losses due to radiation are very low.

In accordance with another embodiment of the invention, the essential structural parts or portions of the pipe lines are located outside the pressure-proof and heat-insulated chamber and are heated, for example, by an external heating unit.

The two embodiments discussed above ensure that the temperature in and at the structural components, which are present in the chamber, is maintained within the desired range of temperature. Outward cold bridges are avoided, with the exception of some few pipe lines present still outside the chamber, which can of course be insulated correspondingly and/or heated separately. With the arrangement according to this invention, not only the functional advantages described are achieved, but also a compact and simple construction arrangement is created from the chamber and the components situated in it, which is an outwardly compact, for example, cylindrical chamber, with some few pipe lines. As the components placed inside the chamber do not have to be insulated and are situated within the chamber under increased pressure, they therefore do not have to be made pressure-proof. This results in an advantage for the arrangement according to this invention having relatively low construction costs.

The hydro-cyclone groups which form a stage can be arranged in a dome which is also pressure-proof and heat insulated. The dome may have a cover which is removable and which supports the corresponding hydro-cyclone group. As a result, it is possible to easily reach the hydro-cyclones of each group for repairs or replacement. Thus, only the cover of the dome has to be taken off and lifted upward with the hydro-cyclones attached thereto. It is to be understood in this connection that whenever a number of hydro-cyclones are mentioned, this is done only for simplicity's sake. In each instance, the situation is to be included where only a single hydro-cyclone is present in each group.

In accordance with a preferred embodiment of the invention, the walls of the chamber and of the domes may be heatable from the outside. In addition to the insulation which is provided, this heating ensures that the temperature in the chamber is maintained constant. This is particularly recommended if the range of temperature to be maintained in the chamber is very low.

In order to provide compensation for thermal stresses, the hydro-cyclones or hydro-cyclone groups may be suspended in the domes by means of expandable parts, for example, bellows. In accordance with another feature of the present invention, the underflows and the overflows of the hydro-cyclone groups and their outlets to the pump wells of the arrangement are situated completely within the chamber or the domes.

On the other hand, it is also possible to provide at least the motors of the pumps and the pump pressure pipe lines partly outside the chamber, with the pump pressure pipe lines being connected to the inlets of the hydro-cyclone groups which follow mixed in the feeding direction of the suspended solids. Also, to each pump well a stirring mechanism is assigned whose motor is located outside the chamber. Thus, the structural components which are sensitive to pressure and/or temperature, such as, the motors of the pumps and stirring mechanisms, are located outside of the chamber.

If the chamber is of elongated shape, the feed of the suspended solids and the discharged overflow of the separating fluid is provided in one end region of the chamber, and the addition of the separating fluid and the waste or outlet of the separated and thickened solids suspension are provided in the other end region. The stages of the countercurrent unit connected in series are situated in between the two end regions.

A hydro-cyclone group each, a dome containing the hydro-cyclone group and a pump each with stirring mechanism, are arranged in the stages of the chamber next to each other, i.e., approximately in a plane extending transversely of the longitudinal direction of the chamber, wherein the pump well is situated in the lower region of each stage, the pump well being separated by cross-walls from each adjacent pump well.

The underflow of the hydro-cyclone group of each stage flows directly downwards into the pump well situated under it.

The overflow of the hydro-cyclone group of each stage flows out directly downwardly into a channel, chute or the like, which is placed in such an inclination that it allows the overflow to flow in feeding direction of the separating fluid in the natural slope to the pump well after the next one or to the pump well of the separating fluid outlet.

The pumps and hydro-cyclone groups are placed on both sides of a vertically extending longitudinal middle plane of the chamber in the sections or stages of the chamber which are situated one after the other in the longitudinal direction thereof, wherein alternately a pump and a hydro-cyclone group, or the dome accommodating the latter, are provided in the longitudinal direction of the chamber, and in each case the pressure pipe line of a pump is connected with the inlet of the hydro-cyclone group or dome placed adjacent in the feeding direction of the suspended solids.

In accordance with another feature of the invention, the height of the separating walls decreases between the pump wells in the direction of feeding of the separating fluid and, thus, makes possible an overflow from one pump well to the pump well next adjacent in the feed direction. As a result, the fluid level in the pump wells has the exact desired value, without requiring complicated regulating instruments, such as, Caesium radiators or the like. Moreover, floater regulating systems known from other apparatus of this type are avoided. These systems would easily mix with the solids to be separated, particularly if crystallizing solids are to be separated. This feature concerning the height of the separating walls is particularly advantageous in conjunction with the overflow of the hydro-cyclone group of each stage which flows out directly downwardly into a channel, chute or the like, as discussed above.

In accordance with a method according to the invention for obtaining a continuous overflow from one pump well to the adjacent pump well, the inlet of separating fluid and the pump performance are adjusted to one another in such a way that always more inflow than pump discharge exists.

Moreover, a specific object is to provide a countercurrent separating unit for suspended solid matters in saturated solutions so that in case of pressures which are above the vapor pressure of the separating fluid at the working temperature, a further crystallization of the solid matters dissolved in the suspension is avoided, on the one hand, with safety, and on the hand, also with an acceptable expenditure with respect to apparatus.

This object is met by using the multistage arrangement for countercurrent separation described above for the treatment of saturated solutions with crystallizing suspended solids for the purpose of avoiding crystallization. In the treatment of such solutions it is of decisive importance to avoid an undesired crystallization of additional solid particles. This additional crystallization could, on the one hand, have the result that the pipe lines, walls of the chamber, chutes and pipe connections, etc. are clogged more or less quickly, and on the other hand, cause an undesired crystallization also from impurities which are contained in the solvent during, for example, the purification of terephthalic acid and should be removed by the separating process. In order to avoid these disadvantages, it must be ensured that a falling below of the vapor pressure belonging to the working temperature of the solvent is avoided in any case during the countercurrent separation. One such falling below alone could be caused, for example, by the suction operation of pumps. It would lead to a corresponding evaporation of the solvent with the consequence of the previously mentioned crystallizations. But this is prevented according to this invention thereby that the pump well from which suction takes place is situated within the chamber placed under pressure.

The same danger exists also when an impermissible decreasing of the working temperature of the undercurrent separation occurs. For example, in the production of terephthalic acid explained in more detail afterwards corresponding to DE-PS No. 30 44 617, the working temperature of the countercurrent separation is a function of the solubility and cocrystallizing tendency of the impurities contained in the solvent, i.e. mother liquor. Such impurities have the tendency to crystallize on the pure terephthalic acid crystals. The working temperature is adjusted in such a way that the terephthalic acid is crystallized as completely as possible on the one hand, while, on the other, the impurities are also dissolved as completely as possible. In this case a falling of temperature would have inevitably again the result that also the impurities would be crystallized in an undesired way with the consequences mentioned previously and, in addition, the above-mentioned danger of clogging occurs.

The countercurrent separation according to this invention makes it possible to obtain faultless results, i.e., a "separated" product having a minimum content of impurities, with comparatively low instrumental cost under relatively extreme requirements regarding pressure and temperature. This is achieved by the fact that this arrangement makes it possible to work readily at a pressure which is above the previously mentioned vapor pressure of the solvent at the working temperature, so that the danger of an impermissible evaporation can be clearly excluded.

In accordance with a preferred embodiment of the invention, the multistage arrangement for countercurrent separation is used for a process of producing pure terephthalic acid. Regarding the details of a possible and preferred process for the production of pure terephthalic acid from dimethyl-terephthalate as intermediate product, reference is made to German patent Nos. 29 16 197 and 30 44 617 mentioned at the outset. In these cases, terephthalic acid is the solid material, water is the solvent (mother liquor), the impurities are mono-methyl-terephthalates and the isomers of the terephthalic acid, and the separating fluid is demineralized water.

Instead of dimethyl-terephthalate as the intermediate product, in accordance with another proposal of the invention, it can be started with crude terephthalic acid as the intermediate product. In that case, terephthalic acid is the solid matter; water, acetic acid or their mixtures again are the solvents; the impurities are para-toluic acid, 4-carboxy-benzaldehyde (4-cba) and the isomers of terephthalic acid and also other impurities which result from oxidation and/or hydrogenating. In both of these preferred cases, a temperature range of less than ±1° C. must be maintained constant. Crystallizations due to cold bridges, for example, are to be avoided by all means.

In accordance with another embodiment of the invention, the multistage arrangement for countercurrent separation can be used for the treatment of an ash-containing very fine coal having a grain size preferably smaller than 1 mm, wherein water is used as the separating fluid and the overflow is the intended product in the form of the further hydrogenable very fine coal fraction suspended in the fluid containing hydrocarbon. Such a carbon hydrogenating occurs at high pressures and temperatures, so that the arrangement provided in accordance with the present invention is significant for the success of such a countercurrent separation.

The various embodiments of the countercurrent separator according to the invention described above are particularly useful when the countercurrent separator is employed for the uses and treatments mentioned above.

In order to prevent problems in situations in which crystals, particularly the crystals of the terephthalic acid, or solids of an ash-containing very fine coal, having an impermissible or undesirable size, an upcurrent separator or upstream classifier may be provided in the countercurrent separator, so that such crystallizations and/or coarser particles can be removed. This upstream classifier is also accommodated in the common pressure-proof and heat-insulated chamber.

Upstream classifiers are known, for example, for separating the grain sizes of sands. However, when utilized in a countercurrent separator, according to the invention, these classifiers have the advantage that any coarser crystals which may be created or any solid particles can be removed. In addition, since the upstream classifier is accommodated in a common, pressure-proof and heat-insulated chamber, the conditions mentioned above concerning the hydro-cyclones etc. are also met with respect to the upstream classifier.

In a process for the production of terephthalic acid, the upstream classifier according to the present invention is provided at the input of the separating fluid. The input of the cleaning separating fluid is connected to its upcurrent opening and forms the upcurrent of the separator. The underflow of the corresponding hydrocyclone or hydro-cyclone group located thereabove is conducted to the inlet of the upstream classifier. The overflow of the upstream classifier flows into the corresponding pump well and is further conducted from there. The underflow of the upstream classifier is closed.

For the treatment of saturated solutions with crystallizing suspended solids, or for the treatment of ash-containing very fine coal, the upstream classifier according to the present invention is provided in the chamber preferably at the outlet of the polluted separating fluid. The upcurrent is formed by a separately supplied separating fluid. The underflow of the corresponding hydro-cyclone or hydro-cyclone group located there-above is supplied to the inlet of the upstream classifier. The overflow of the upstream classifier flows into the corresponding pump well and is further conducted from there. The underflow of the upstream classifier is opened for discharging the separated crystals or solid particles.

The quantity of the clean separating fluid supplied per unit of time and forming the upcurrent may be adjusted in such a way that any crystallization of the terephthalic acid is dissolved at least to such an extent that its size is equal to or smaller than a predetermined maximum size.

The supplied quantity of upcurrent fluid may be regulated or controlled in dependence upon the respective suspension, or its degree of impurity, or any created crystallizations.

The degree of dissolution and/or the particle size to be separated may be influenced by measuring the suspension density in the upstream classifier bed and a corresponding change in the amount of separating water. This can be done by regulating or controlling the suspension supply.

In the case of constant grain size of the components of the suspension supply, the suspension supply may be regulated in dependence upon its density.

The various features of novelty which characterize the invention are pointed out with particularity in the claims annexed to and forming a part of this disclosure. For a better understanding of the invention, its operating advantages and specific objects attained by its use, reference should be had to the drawings and descriptive matter in which there are illustrated and described preferred embodiments of the invention.

DETAILED DESCRIPTION OF THE INVENTION

Figure 1:
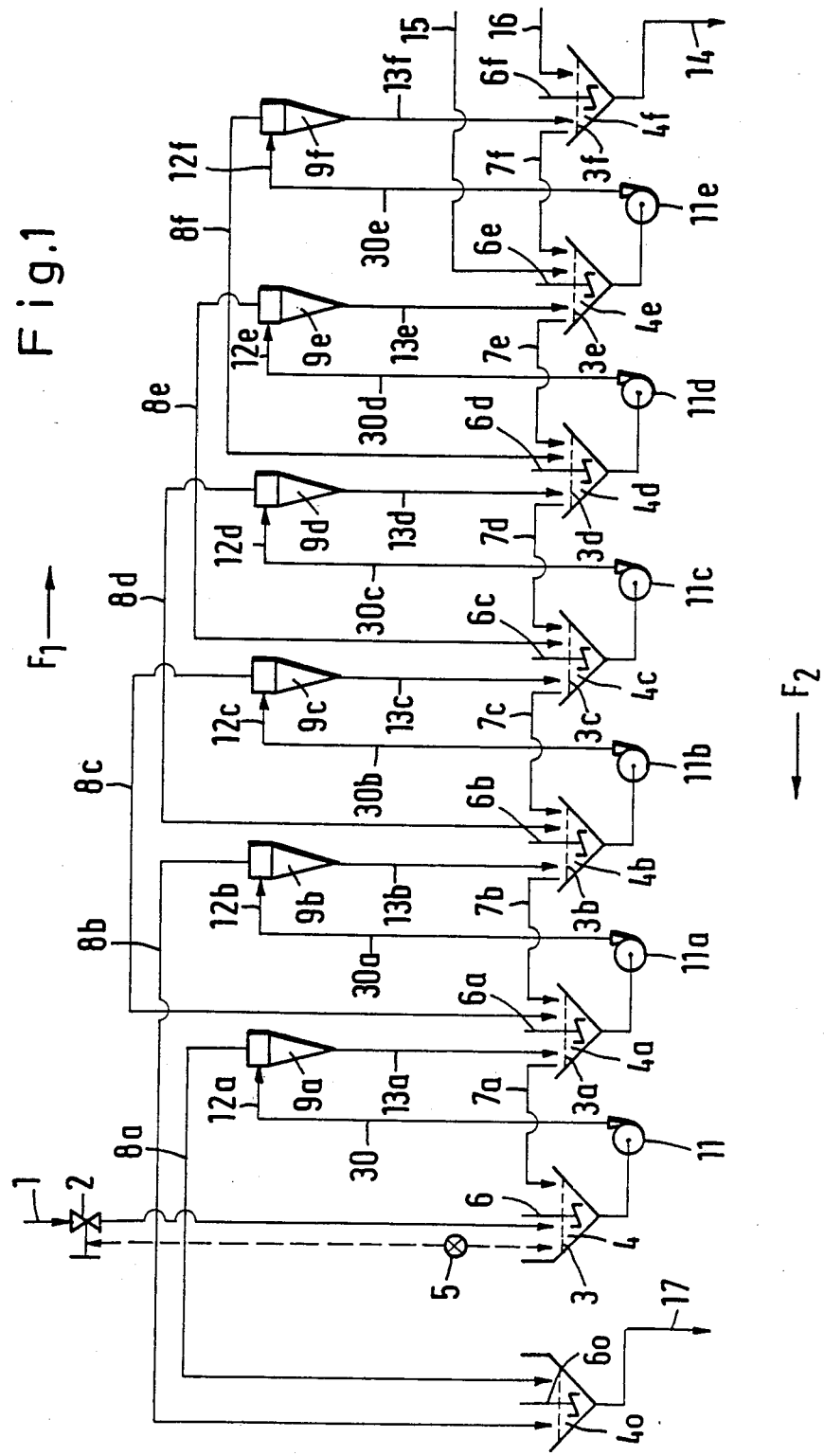
FIG. 1 is a schematic flow chart of the countercurrent separator according to the invention.

At first, the feeding directions of the flow and current patterns, etc. in the countercurrent separating unit are explained with the help of FIG. 1. The polluted suspension flows in through the pipe line 1 and can be regulated by a valve 2 depending on the fluid level 3 of a pump well 4 (preliminary stage). This regulating is done by means of an equipment 5, which is indicated only schematically. This equipment measures the height of the level 3 by radioactive rays, for example. Apart from the polluted suspension 1, also the overflow 7a of the next following pump well 4a is conducted into the pump well 4. The content of the pump well 4 is conducted over a pump 11 and a pipe line 30 to the inlet 12a of the following hydro-cyclone group 9a in the feeding direction F1 of the suspension. The underflow 13a of hydro-cyclone group 9a reaches the corresponding pump well 4a with stirring mechanism 6a. In this pump well 4a is directed in the feeding direction F2 of the separating fluid the overflow 7b of the pump well 4b following in the feeding direction F1 and the overflow 8c of the hydro-cyclone group 9c after the next in the feeding direction F1. This goes on correspondingly through the several steps of the countercurrent separating unit consisting of hydro-cyclone groups, pump wells with pumps and stirring mechanism. In this process the suspension is thickened again and again step by step and thus purified more and more until it flows out finally at 14 from the pump well 4f of the last step. The separating fluid is added at 15 in the flow direction F2 and flows over the overflows 7a to 7e. At 16 a filtrate can be added. In addition the overflows of the pump wells 4f, 4e, etc. flow in natural slope according to numerals 7f, 7e, etc. in the feeding direction F2. Similar to the components explained previously, also the underflows of the hydro-cyclone groups 9a, 9b, etc. are numbered with 13a, 13b, etc. and their overflows 8a, 8b, etc. They flow into the pump wells 4a, 4b, etc. situated underneath in each case. The mixing of the thickened cyclone underflow and the overflow transferred into it takes place in the pump wells.

The end region situated at the left in FIG. 1 contains not only the suspension supply 1 mentioned at the outset, but also the discharge, i.e. underflow, 17 of the polluted separating fluid from a pump well 40. The overflows 8a and 8b of both hydro-cyclone steps placed next in the feeding direction F1 lead into this pump well 40. The other end region situated to the right in FIG. 1 contains the outlet 14 of the purified and thickened suspension already explained and the above-mentioned feed pipes 15, 16.

Figure 2:
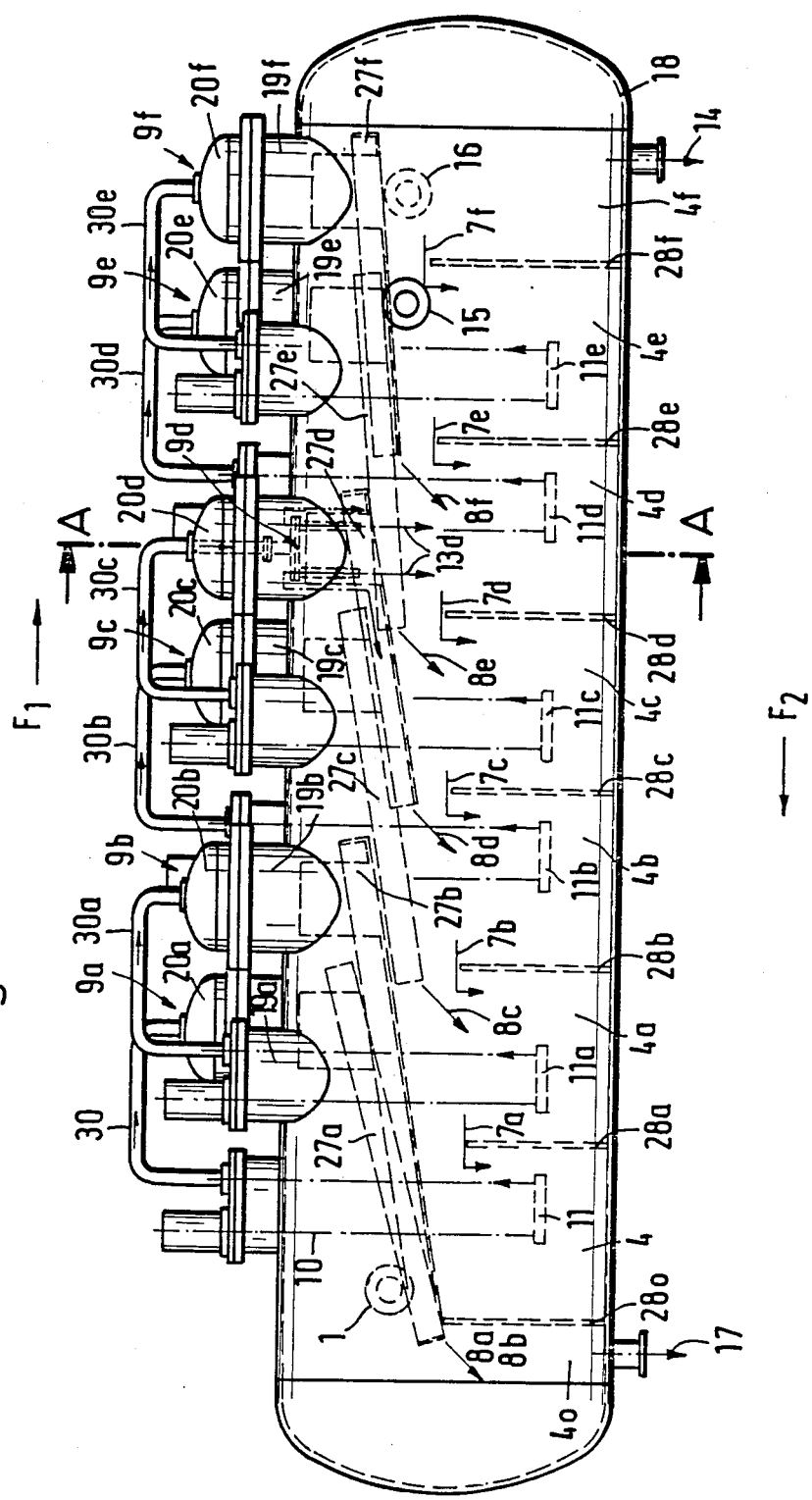
FIG. 2 is a side view of the arrangement according to the invention.
Figure 3:
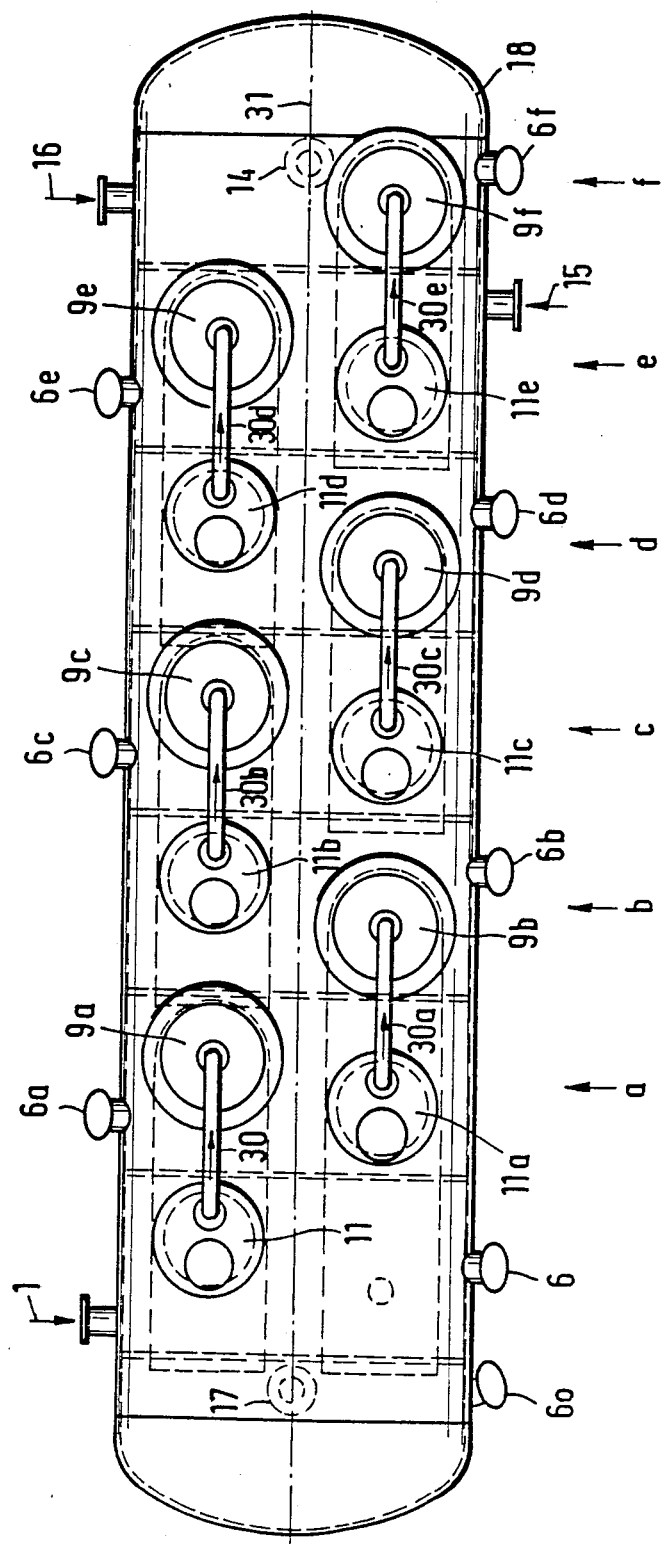
FIG. 3 is a top view of the arrangement of FIG. 2.
Figure 4:
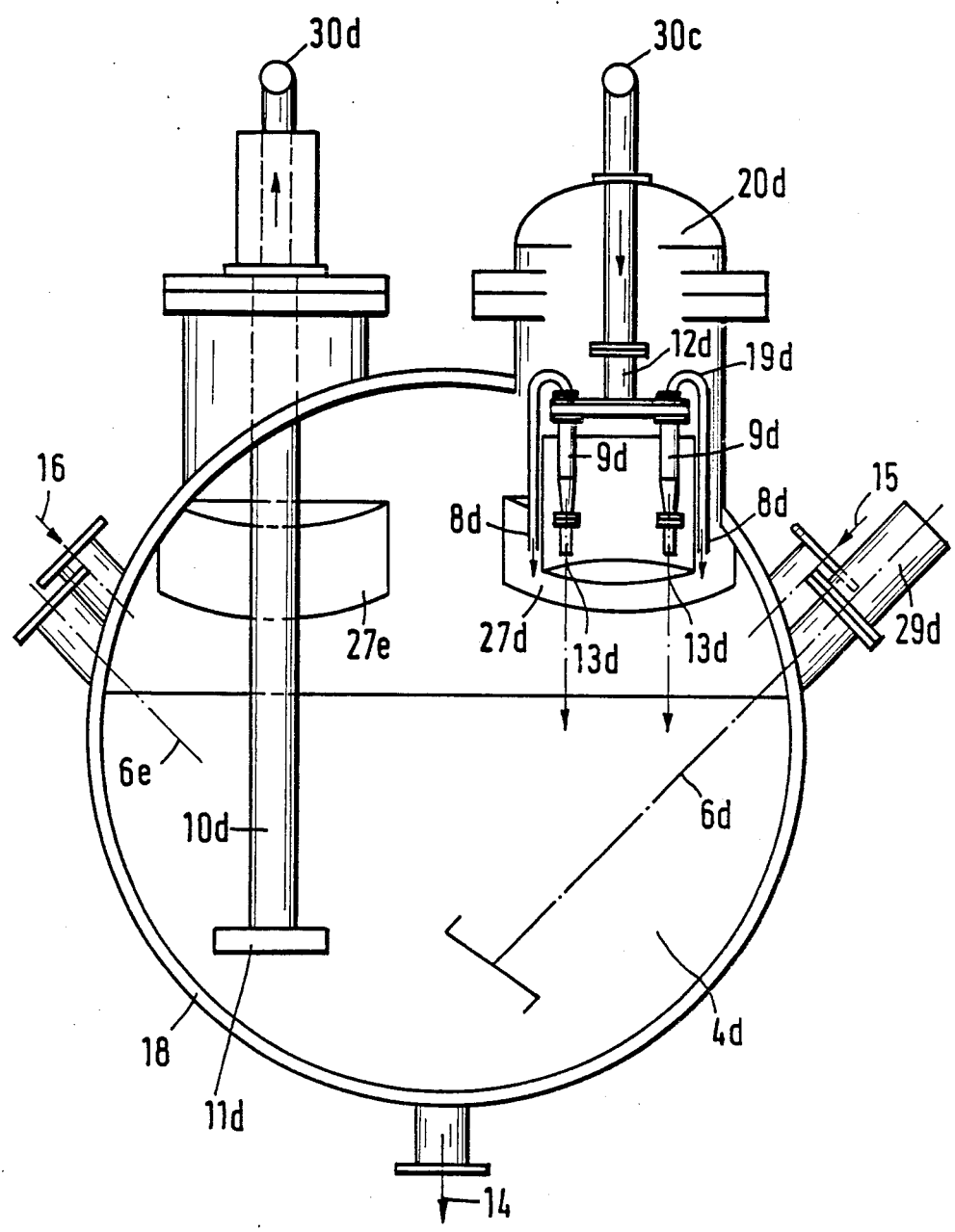
FIG. 4 is a sectional view taken along line A—A in FIG. 2.

The elements of this countercurrent separating unit explained in FIG. 1 are marked with the same numerals in FIGS. 2 to 4. A chamber 18 surrounding mostly these elements is pressure-proof and heat-insulated. Pressures in the magnitude of 75 bar and temperatures as high as 300° C. can appear when the arrangement according to this invention is operated. These statements are made of course only as an example, without the invention being restricted to these. Each hydro-cyclone group 9 is arranged in this preferred embodiment in a dome. The dome consists of a lower part 19a to 19f connected rigidly with the chamber 18 and of an upper part (cover) 20a to 20f releasably connected, preferably flanged with it. After releasing the flange connection and the feed pipe 12, if required, the respective upper part of the dome 20a to 20f with the hydro-cyclones suspended therefrom can be lifted upward for the purpose of exchanging or repair of the hydro-cyclone and then subsequently can be placed back on the corresponding lower part of the done 19a to 19f and can be connected rigidly with it.

Figure 5:
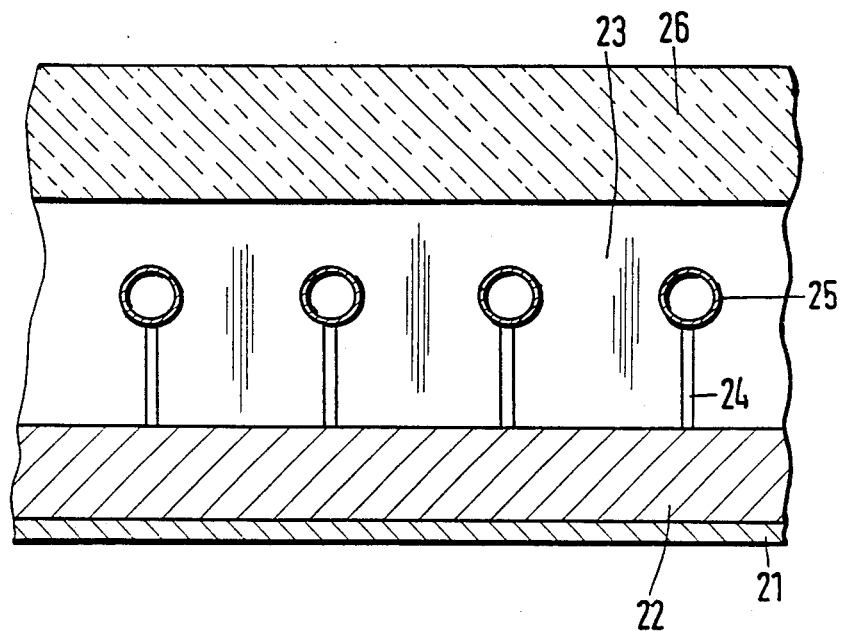
FIG. 5 is a sectional view of the wall of the chamber of the arrangement on a larger scale.

FIG. 5 shows a section from the chamber wall and the dome wall on a larger scale consisting of an inner protection layer 21 of for example high grade steel 1.4571 or titanium or any other corrosion proof substance. DIN 1.4571 is an internationally known designation. It designates an austenitic steel of the composition: Si 1.0; Mn 2.0; P 0.045; S 0.030; Cr 16.50–18.50; Mo 2.00–2.50; Ni 11.00–14.00 and C≦0.08. If the carbon content is smaller than 0.03, such a steel is stabilized; otherwise it would have to be stabilized, for example, by means of titanium. Basically, chromium-nickel steels of the type X 10 Cr Ni 18 8 of austentitic structure can also be used. Similar and corrosion-technologically equivalent steels are known under the U.S. designation 316 L. However, the above statements are made only as examples without the invention being restricted to them. The load bearing steel shell 22 is attached to inner layer 21. An air gap 23 follows in the outward direction where a heating unit 25 held by webs 24 is located. Heating unit 25 is heated by steam flowing through pipes, for example. 26 is the insulating layer lying outside. Heating and insulation are matched with each other.

FIG. 2 and FIG. 4, drawn on a bigger scale compared to FIG. 2, show that the underflows 13a to 13f and the overflows 8a to 8f of the hydro-cyclone groups and their pipe connections to the pump wells 4 to 4f are completely inside the chamber 18 or the domes 19a to 19f, 20a to 20f. The underflows 13a to 13f flow directly into the pump wells 4a-4f situated below those. The overflows of the hydro-cyclone groups flow into the channels, chutes or the like 27a to 27f situated below those. These channels, etc. correspond to the pipe lines 8a to 8f of FIG. 1 in function. These channels, chutes or the like are inclined downward in the feeding direction F2 and are arranged in such a way that they allow the overflow of the separating fluid in the natural slope either through the channels, chutes or the like 27b to 27f into the pump well after the next one or, in case of channel, chute or the like 27a, into the pump well 40 of the region lying to the left in FIG. 2. Each of the pump wells 4 to 4f are separated from each other by separating walls 28f to 28a. The separating walls are to a certain extent lower in each case in the feeding direction F2. Moreover, it is ensured that the feed of separating fluid 15 and the respective pump performances are matched with each other in such a way that the whole inflow of fluid into the respective pump well is always greater than the suction of the pump. Thus, the pump wells are filled always up to the edge of the separating wall 28 situated in the feeding direction F2 of the separating fluid, i.e., the height of the level of the wells is regulated always at a constant value. The overflowing fluid flows according to the pipe line characteristics 7f to 7a in feeding direction F2 of one pump well to the next one following. Floater regulation or similar means are not necessary, as indicated. The separating wall 28o between the pump wells 4 and 4o is however made deliberately higher as at this position no overflow should take place. An idle running of the pumps is avoided due to the reasons mentioned earlier. The driving motors of the pumps 11 to 11f and 29 to 29f of the stirring mechanism are situated preferably outside the chamber, so that they are not subjected to the high pressure present inside the chamber and the high temperature there. The pumps may either be submerged pumps, and, thus, be provided completely within the chamber 18. It is also possible to provide a portion of the pumps on the outer side of the chamber and to heat them there, while the remaining parts of the pump project into the chamber, i.e., in the respective pump well.

FIGS. 2, 3 show further that the pump pressure pipe lines 30 to 30e are connected to the inlet of the hydro-cyclone group following as the next in the feeding direction F1 of the suspended solid matters. Also, at this place it is pointed out that to one hydro-cyclone group belongs either only a single hydro-cyclone or several hydro-cyclones connected parallel to each other. The pump pressure pipe lines are heat-insulated. While the pipe lines are provided outside of the chamber and are heated in order to avoid crystallizations, i.e., are heated separately (not illustrated in the drawing), in accordance with a preferred embodiment of the invention, the pipe line portions located outside the chamber are to be kept as short as possible, so that they are with greater portions of their lengths located within the chamber. It is also possible to provide only portions of the pumps in chamber 18. Therefore, the portions of the pumps and the pipe lines located outside the chamber which conduct media to be kept at a certain temperature, are heat-insulated and/or heated separately. In addition, in accordance with FIG. 3, the arrangement can be made as follows: at both sides of the vertical plane 31 stretching in the longitudinal direction of the chamber 18, a pump and a hydro-cyclone group are placed alternately one after another. In each of the steps, i.e., approximately transversely of the direction of the longitudinal middle plane 31, there are a pump and a hydro-cyclone group near each other. In addition to the hydro-cyclone group of the step a to the left in FIG. 3 and to the right of the pump of the step e, a hydro-cyclone group is situated at f. With this arrangement of space, the required length of the pump pressure lines 30 to 30e is kept as short as possible. The pump wells, which have already been explained, are situated in the lower regions of these steps. The pump shafts are numbered by 10.

Various possibilities of application of this invention have been discussed above. One further possibility of application of this invention, where no saturated solution is provided with crystallizing suspended solid matters, is described below:

A hydrocarbon suspension containing-ash containing very fine coal with grains smaller than 1 mm is separated at high pressure (e.g. 60 bar) and high temperature (e.g. 200° C.) with least possible water in the countercurrent according to the method which has already been described. The separation results thereby in the ash-rich and also specifically heavier and coarser water containing fraction (underflow), on the one hand, and in the hydrogenizable very fine coal fraction (overflow), on the other, which is suspended in the fluid containing hydrocarbon. In this case of application, the overflow is the desired, i.e. intended, product, whereas the underflow, i.e. the carbon product rich in ash with some water, represents the waste product.

This example shows therefore the countercurrent separation of non-crystalline solid matters, on the one hand, and, on the other, that the arrangement according to this invention can also be used in such a way that the overflows lead to the desired end product and the underflows to the waste product.

Figure 6:
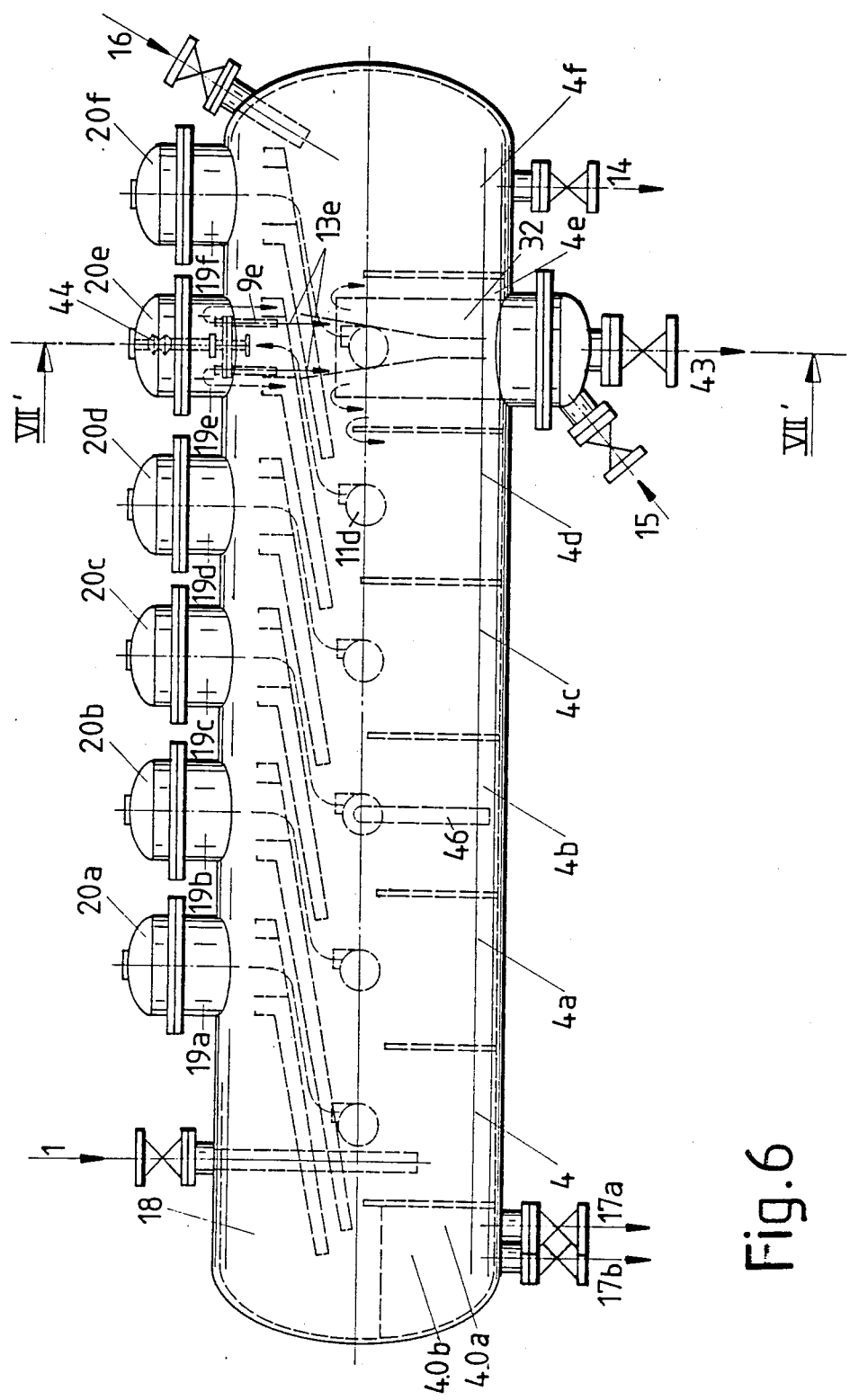
FIG. 6 is a flow chart as in FIGS. 1 and 2, however, the flow outlets and connections already illustrated in FIGS. 1 and 2 are not shown, while an upstream classifier used at the beginning of the feed of the separating fluid is illustrated.
Figure 7:
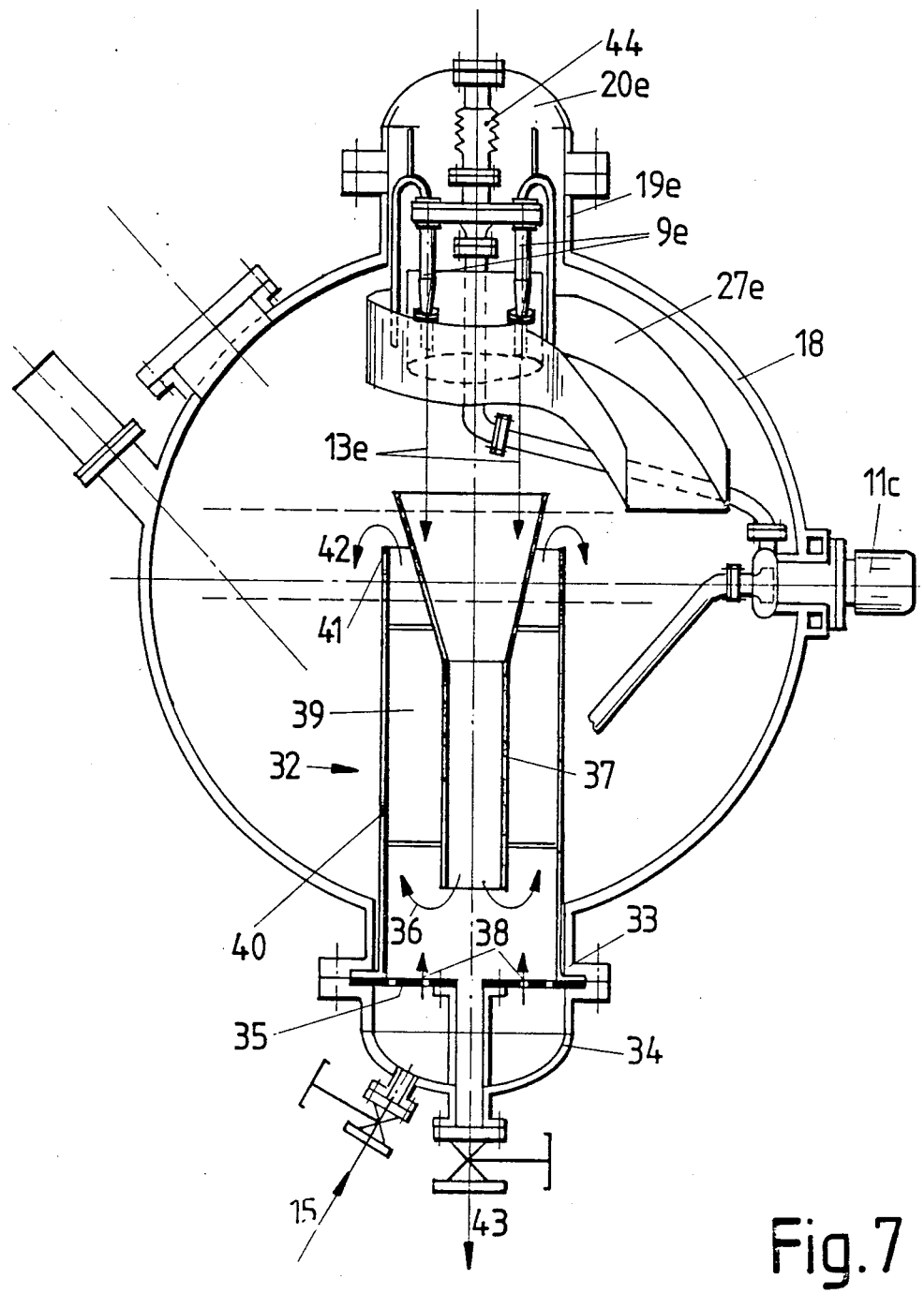
FIG. 7 is a sectional view taken along line VII—VII in FIG. 6.

The schematic illustration of FIG. 6 shows, with details already explained being omitted, an upstream classifier 32 which in this undercurrent separating sequence is provided in the pump well 4e and underneath the hydro-cyclone group 9e in such a way that the input of the fresh feed of separating fluid 15 simultaneously is the upcurrent water of this separator. As particularly illustrated in FIG. 7, this classifier is essentially located within the chamber 18. To the extent that it still projects out of chamber 18, a pressure-proof and heat-insulated dome 33, 34 is provided. Removable dome part 34 makes it possible to introduce the upstream classifier through connecting piece 33 to chamber 18 and to remove it therefrom. The upcurrent 15 flows through a nozzle plate 35 and meets the thickened suspension 13e of the underflows of the hydro-cyclone groups 9. As indicated by arrows 36, this thickened supsension is discharged from the lower end of a pipe piece 37 leading into the underflow 13e and is entrained upwardly by the upcurrent 38 and is conducted to overflow 41 of the upstream classifier through the upcurrent separating bed 39 in the form of an annular space which is located between the outer wall 40 of the classifier and its pipe 37. If the arrangement is used for a process for production of terephthalic acid, the crystals of the terephthalic acid which are too large or too coarse can be dissolved by the upcurrent and, thus, reduced in their size until the desired or permissible maximum size is reached. This may be, for example, a crystal size of $250\mu$. The crystals of the desired reduced size are then conducted according to arrows 42 over the overflow edges 41 into the pump well 4e, and from there into the next following pump well, etc., as has been explained in detail with the aid of FIGS. 1 and 2. In the above-mentioned case of application of the production of terephthalic acid, the upstream classifier must be arranged within the countercurrent separating unit in such a way (see for example FIG. 6) that the upcurrent is formed by fresh separating fluid which is not yet polluted. Otherwise, the desired reduction of the coarser crystals would not be obtained at all or only to a very incomplete extent. Even if a substantial portion of the coarse crystals of the terephthalic acid has been reduced as explained above and is discharged upwardly with the upcurrent, it is still necessary to provide a discharge or outlet 43 at the upstream classifier. This is because the upcurrent water and, thus, the solubility and desired crystal reduction cannot always be kept at an exact equilibrium. Therefore, it must be possible to discharge crystals which are too coarse through outlet 43. It is also to be pointed out that the reduction of the crystals of the terephthalic acid must be effected by means of fresh, unsaturated water because otherwise the effect of dissolution or reduction of these crystals cannot be achieved.

Figure 8:
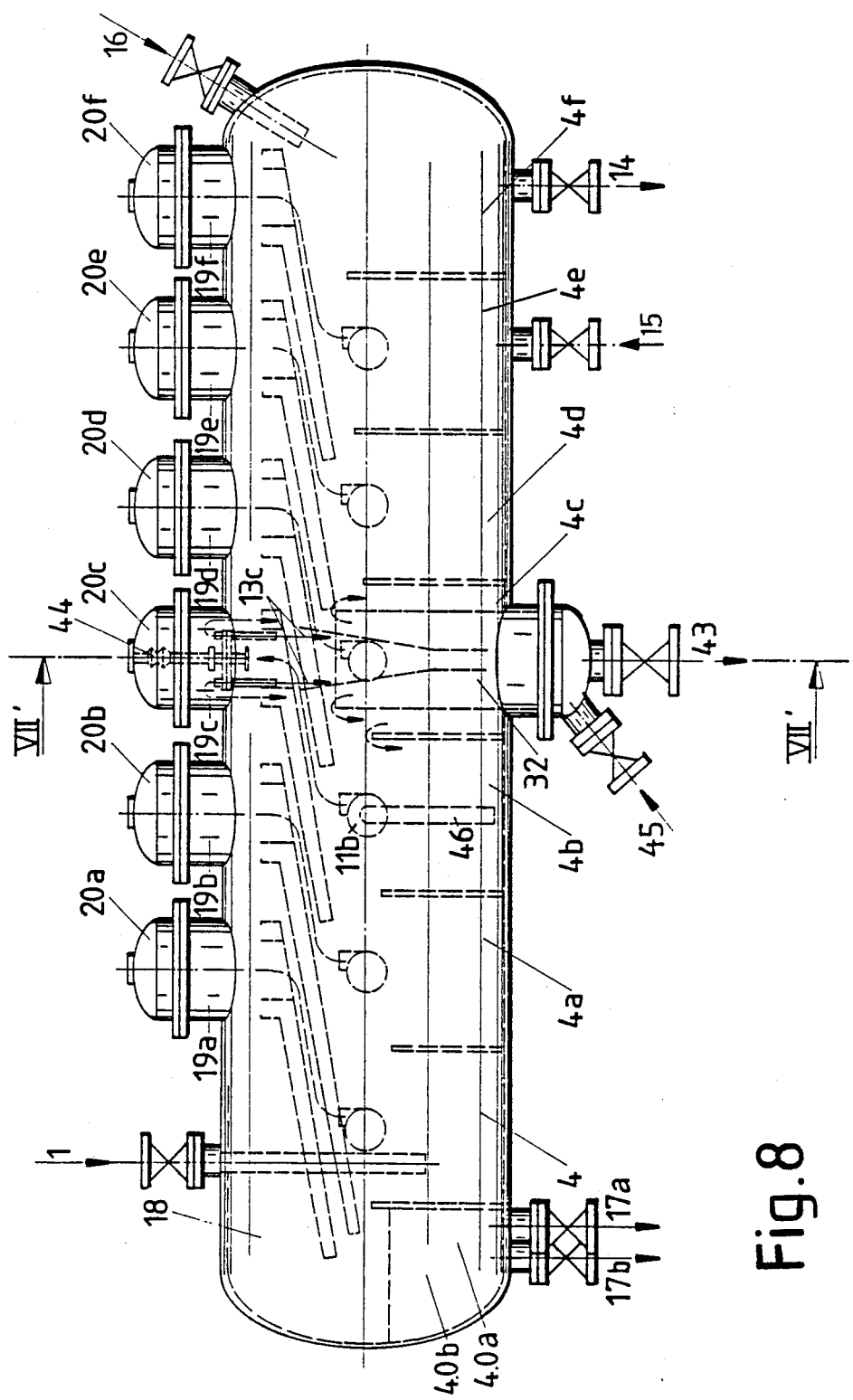
FIG. 8 is a flow chart as in FIG. 6, however, with the upstream classifier arranged at a different location of the chamber.

If in other cases of application crystals are to be found or formed in the suspension, or if solid particles are present which due to their size are troublesome but cannot be dissolved, these crystals or solid particles can also be removed by means of an upstream classifier. This is shown by the embodiment according to FIG. 8, wherein section VII'—VII' practically corresponds to section VII—VII of FIG. 6 and, thus, of FIG. 7. Also in this case, the discharge opening 43 is provided for the discharge of the crystals or solid particles to be separated. However, in this case, it is not necessary to use fresh, unsaturated upcurrent water. Therefore, the upstream classifier can be provided at any chosen location of the flow sequence in chamber 18, for example, in pump well 4c, as shown in FIG. 8. In this case of application, no dissolution or reduction of crystals takes place, but only a separation of particles or grains which are too coarse which separating can also be done by a polluted liquid. However, preferably the upstream classifier used for separation will be provided in the pump well 4e, i.e., at the location where the fresh separating fluid is supplied. The operation of the upstream classifier in the embodiment according to FIG. 8 shall now be explained as follows, essentially with the use of the reference numerals of FIG. 7:

Upcurrent water is supplied at 45. The underflow 13c flows from hydro-cyclone group 9c into pipe piece 37 and, after being discharged at the lower end of the pipe piece, is entrained by upcurrent 38 where the separation takes place. In this example, however, the crystals or solid particles which are too large or too coarse are not partially dissolved, but fall downwardly and are discharged through discharge pipe 43. The overflow 42 is conducted into pump well 4c in which the upstream classifier is located. The sequence of the countercurrent separation is otherwise the same as described with the aid of FIGS. 1 and 2. The various possibilities of arranging the upstream classifier in container 18 are already described above. If particles which are too coarse are to be removed by separation from an ash-containing very fine coal, it is recommended to provide the upstream classifier as far as possible toward the output side of the separating fluid, i.e., preferably in pump well 4a.

The hydro-cyclone group can be elastically suspended in the cover (20e or 20c) of the respective dome through a bellows 44. This has the advantage that thermal tensions can be absorbed or compensated by the bellows. This bellows or another elastically expanding member supports the hydro-cyclone distributor. In addition, an inlet (pipe line) to the distributor can be conducted through such a bellows.

Concerning the control or regulation it is additionally pointed out the degree of dissolution and/or the particle size to be separated from the suspension can be influenced by measuring the suspension density in the upstream classifier 39 (FIG. 7) and an appropriate change in the quantity of the upcurrent water.

In order to obtain a uniform grain size in the final product, in the case of a constant grain size of the suspension supplied at 1, it is sufficient to regulate the suspension supply in dependence on the density of this suspension which is measurable.

FIG. 8 additionally shows a suction pipe line 46 which is provided on each of the pumps (in this case, pump 11b, not illustrated in detail). This line serves for pumping the suspension from the pump well even when the liquid level is low.

Figure 9:
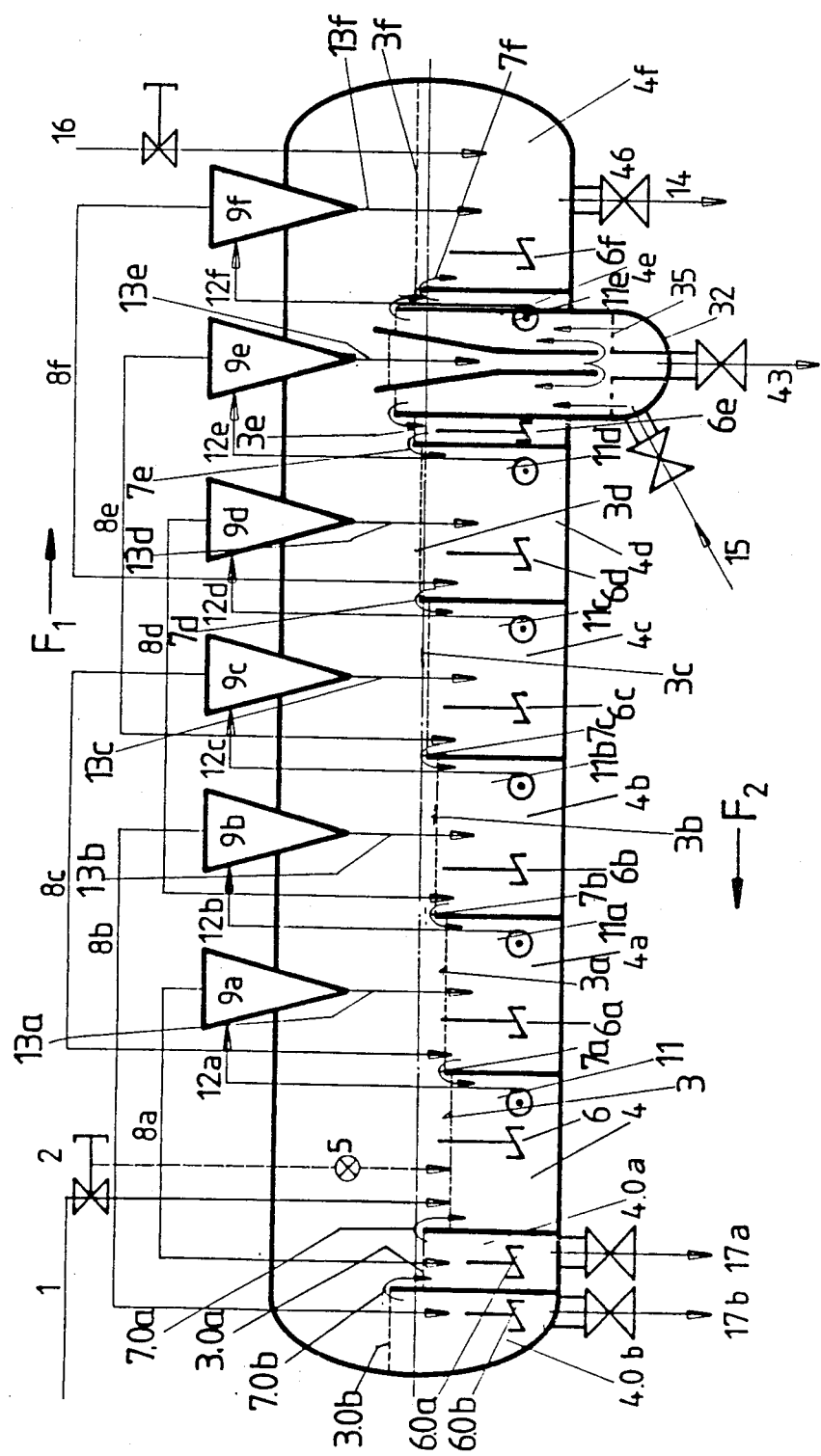
FIG. 9 is a schematic illustration of the flow sequence of an arrangement according to FIG. 6 with a variation of the discharge of the polluted separating fluid. This flow chart is applicable also to the embodiment according to FIG. 8, with the difference that the upstream classifier is to be provided at the location according to FIG. 8.

FIG. 9 shows for a better understanding a flow chart of the embodiment according to FIG. 6, wherein essentially the representation and particularly the reference numerals of FIG. 1 are used. FIG. 9 additionally shows a variation of two separate underflows 17a and 17b of the polluted separating fluid.

The examples of FIGS. 6 to 9 further show that in step 0, the chamber or the pump well 4o can be divided into two chambers or wells 4.o a and 4.o b. Details of this division can be seen particularly from FIG. 9 and the corresponding reference numerals By this means, the overflows 8a and 8b of the hydro-cyclone steps 9a and 9b can be collected separately and, thus, can be supplied separately to different further processing steps. This may be of advantage because the overflows have different degrees of pollution. The overflow 8a is more polluted than overflow 8b. Thus, overflow 8a of hydro-cyclone group 9a leads into pump well 4.o a. The latter is assigned to a separate underflow 17a. On the other hand, overflow 8b of hydro-cyclone group 9b leads into pump well 4.o b whose underflow of the polluted separating fluid is denoted with 17b. It is to be stated generally with respect to all embodiments that fresh separating fluid or separating water must be supplied at 15. If it is necessary, a diluting liquid (filtrate) can be supplied at 16 in order to render the suspension in the chamber or well 4f pumpable, i.e., to dilute the suspension as required.

If a classifier is provided, in the embodiment illustrated in FIG. 6, the upcurrent fluid is identical to the separating fluid. By contrast, in the example of FIG. 8, separating fluid is supplied at 15 and a separate upcurrent fluid or upcurrent water is supplied at 45.

All features which have been illustrated and described, and combinations thereof, are essential for the invention.

While specific embodiments of the invention have been shown and described in detail to illustrate the application of the inventive principles, it will be understood that the invention may be embodied otherwise without departing from such principles.

We claim:

1. A multistage arrangement comprising: means for countercurrent separation of suspended solids having phisical properties similar to terephthalic acid, including groups of one or more hydro-cyclone separators connected parallel to each other, each group of hydro-cyclone separators defining a stage, the hydro-cyclone separator groups being arranged in series and including corresponding pumps and pump wells, and pipe lines connecting the hydro-cyclones, pumps and pump wells, means for feeding separating fluid in the countercurrent to the direction of feeding of the suspended solids, and means for treating suspended solids are under increased pressure and a substantially constant temperature, and a common, pressure-proof and heat-insulated vessel defining a chamber for housing the hydro-cyclone groups, the pump wells and the pump or pump components projecting into the wells.

2. The arrangement according to claim 1, wherein the essential portions or regions of the lines are also placed in the common, pressure-proof and heat-insulated chamber.

3. The arrangement according to claim 1, wherein portions of the pumps and the essential portions or regions of the lines are placed outside of the pressure-proof and heat-insulated chamber and wherein the components placed outside the chamber are additionally heated by an external heating unit.

4. The arrangement according to claim 1, comprising domes in which each hydro-cyclone group belonging to a stage is placed, each dome including a cover which is removable and supports the corresponding hydro-cyclone group, wherein the domes are also pressure-proof and heat-insulated.

5. The arrangement according to claim 4, wherein the walls of the dome can be heated from the outside.

6. The arrangement according to claim 4, comprising expandable means for suspending the hydro-cyclone groups.

7. The arrangement according to claim 6, wherein the expandable means are bellows.

8. The arrangement according to claim 4, wherein the hydro-cyclone groups include underflows and overflows whose outlets to the pump wells of the arrangment are situated completely within the domes.

9. The arrangement according to claim 4, wherein the chamber is elongated having first and second end regions, the feed of the suspended and the discharged overflow of the separating fluid being provided in the first end region, and the addition of the separating fluid and the outlet of the separated and thickened solid matter suspension being provided in the second end region, wherein the stages of the countercurrent separator connected in series are situated between the end regions.

10. The arrangement according to claim 9, wherein a hydro-cyclone group each, or a dome containing this hydro-cyclone group and a pump each, with stirring mechanism are arranged in the stages of the chamber next to each other approximately in a plane extending transversely to the longitudinal direction of the chamber, wherein each pump well is situated in the lower region of each stage, each pump well being separated by cross-walls from each adjacent pump well.

11. The arrangement according to claim 10, wherein the underflow of the hydro-cyclone group of each stage flows directly downwards into the pump well situated under it.

12. The arrangement according to claim 10, wherein the overflow of the hydro-cyclone group of each stage flows out directly downwardly into a channel or chute, which has such an inclination that it allows the overflow to flow in feeding direction of the separating fluid on a natural slope to the pump well after the next one or to the pump well of the separating fluid outlet.

13. The arrangement according to claim 10, wherein the stages are situated in the chamber one after the other in the longitudinal direction thereof, and hydro-cyclone groups being placed on both sides of a vertically extending longitudinal middle plane of the chamber, wherein alternately a pump and a hydro-cyclone group or the dome accommodating the latter, are provided in the longitudinal direction of the chamber, and the pressure pipe line of each pump is connected with the inlet of the hydro-cyclone group or dome placed adjacent thereto in the feeding direction of the suspended solids.

14. The arrangement according to claim 10, comprising separating walls between the stages, wherein the height of the separating walls decreases between the pump wells in the direction of feeding of the separating fluid, so that an overflow exists from one pump well to the pump well placed adjacent in the feed direction.

15. The arrangement according to claim 1, wherein the walls of the vessel can be heated from the outside.

16. The arrangement according to claim 1, wherein the hydro-cyclone groups include underflows and overflows whose outlets to the pump wells of the arrangement are situated completely within the chamber.

17. The arrangement according to claim 1, wherein at least the motors of the pumps, and particularly the pump pressure pipe lines are situated outside the chamber, the pump pressure pipe lines being connected to the inlets of the hydro-cyclone groups following next in feeding direction of the suspended solids.

18. The arrangement according to claim 1, comprising stirring mechanisms assigned to each pump well, the motors of each stirring mechanism being situated outside the chamber.

19. The arrangement according to claim 1, comprising means for introducing filtrate as necessary wherein the inlet for the separating fluid and the means for introducing filtrate and the pump performance of each pump well are adjusted to one another in such a way that always more inflow into the respective pump well than pump discharge exists.

20. The arrangement according to claim 1, wherein a stage located at the end of the chamber in the flow direction of the separating fluid is divided into two chambers or pump wells wherein a separate underflow of the polluted separating fluid belongs to each of these pump wells, and the overflows of the hydro-cyclone stages are each conducted into the corresponding pump wells.

21. The arrangement according to claim 1, comprising an upstream classifier in the sequence of the countercurrent separation, for removing crystallization and coarser solid particles, wherein the upstream classifier is accommodated in the common pressure-proof and heat-insulated chamber.

22. The arrangement according to claim 21, wherein the upstream classifier is arranged in a dome, the cover of the dome being removable, and the dome being pressure-proof and heat-insulated.

23. The arrangement according to claim 24, wherein the upstream classifier is provided at the input of the separating fluid, comprising connecting means for connecting the input of the clean separating fluid to the upcurrent opening, the input forming the upcurrent of the classifier, means for conducting the underflow of the corresponding hydro-cyclone group located thereabove to the inlet of the upstream classifier, means for conducting the overflow of the upstream classifer into the corresponding pump well and further from there, wherein the underflow of the upstream classifier is closed.

24. The arrangement according to claim 24, wherein the upstream classifier in the chamber is provided at the outlet of the polluted separating fluid, comprising means for supplying upcurrent formed by a separately supplied separating fluid, means for supplying the underflow of the corresponding hydro-cyclone group located thereabove to the inlet of the upstream classifier, means for conducting the overflow of the upstream classifier into the corresponding pump well and further from there, wherein the underflow of the upstream classifier is opened for discharging the separated crystals or solid particles.

* * * * *